United States Patent [19]
Butterworth et al.

[11] Patent Number: 6,130,956
[45] Date of Patent: Oct. 10, 2000

[54] CONTINUOUS MICROBIOTAL RECOGNITION METHOD

[76] Inventors: Francis M. Butterworth, 920 Ironwood Dr., 344, Rochester, Mich. 48307; Manohar Das, 1723 Hillcrest Dr., Rochester, Mich. 48306

[21] Appl. No.: 09/024,184

[22] Filed: Feb. 17, 1998

[51] Int. Cl.[7] .................................................. G06K 9/00
[52] U.S. Cl. .......................................... 382/100; 382/133
[58] Field of Search ................................... 382/100, 128, 382/133, 155, 190, 226, 275; 348/79, 81; 356/39; 250/564, 565, 573, 576, 430, 431

[56] References Cited

U.S. PATENT DOCUMENTS

| | | | |
|---|---|---|---|
| 4,199,748 | 4/1980 | Bacus | 340/146.3 CA |
| 4,661,845 | 4/1987 | Saito et al. | 358/99 |
| 4,821,336 | 4/1989 | Roye | 382/56 |
| 5,224,036 | 6/1993 | Ito et al. | 364/413.13 |
| 5,229,849 | 7/1993 | Pleass et al. | 358/93 |
| 5,313,532 | 5/1994 | Harvey et al. | 382/15 |
| 5,544,265 | 8/1996 | Bozinovic et al. | 382/203 |
| 5,550,933 | 8/1996 | Stetten | 382/199 |
| 5,561,718 | 10/1996 | Trew et al. | 382/118 |
| 5,627,907 | 5/1997 | Gur et al. | 382/132 |
| 5,638,459 | 6/1997 | Rosenlof et al. | 382/133 |
| 5,841,884 | 11/1998 | Yamamoto | 382/110 |

FOREIGN PATENT DOCUMENTS

| | | | |
|---|---|---|---|
| 5-72199 | 3/1993 | Japan | G01N 33/18 |
| 6-27014 | 2/1994 | Japan | G01N 15/06 |

OTHER PUBLICATIONS

Zhu et al., "A Transformation–Invariant Recursive Subdivision Method for Shape Analysis," *IEEE Proc. 9th Int.Conf. on Pattern Recognition*, 1988, pp. 833–835.

Kiryati, "Calculating Geometric Properties of Objects Represented by Fourier Coefficients," *IEEE Proc. Computer Society Conf. on Computer Vision and Pattern Recognition*, 1988, pp. 641–646.

Aloimonos, "Visual Shape Computation," *Proc. of the IEEE*, vol. 76, No. 8, Aug. 1988, pp. 899–916.

Shen et al., "Application of Shape Analysis to Mammographic Calcifications," *IEEE Transactions on Medical Imaging*, vol. 13, No. 2, Jun. 1994, pp. 263–274.

Das et al., "Statistical Signal Modeling Techniques for Automated Recognition of Water–Borne Microbial Shapes," *IEEE 39th Midwest Symp. on Circuits and Systems*, 1997, pp. 613–616.

*Primary Examiner*—Andrew W. Johns

[57] ABSTRACT

A method to continuously identify and recognize microbiota in water comprises random sampling of a water source, directing the sample to an optical plane where microscopic CCD/video images are obtained and stored in analogue and digitized form. Statistical data on organism type and number will be simultaneously collected. Using novel software the digitized images are filtered and segmented. Segmented images will activate software to extract morphological and motion-related features. The extracted features are used to search a database for matching, specific microbiota profiles in a recognition and classification step. Software will enable classification, together with the statistical data will ascertain the biological status of the water. A flizzy-logic decision tree will trigger actuator/annunciator relays that manipulate water intake valves and send signals through modems for telephone warning messages.

1 Claim, 1 Drawing Sheet

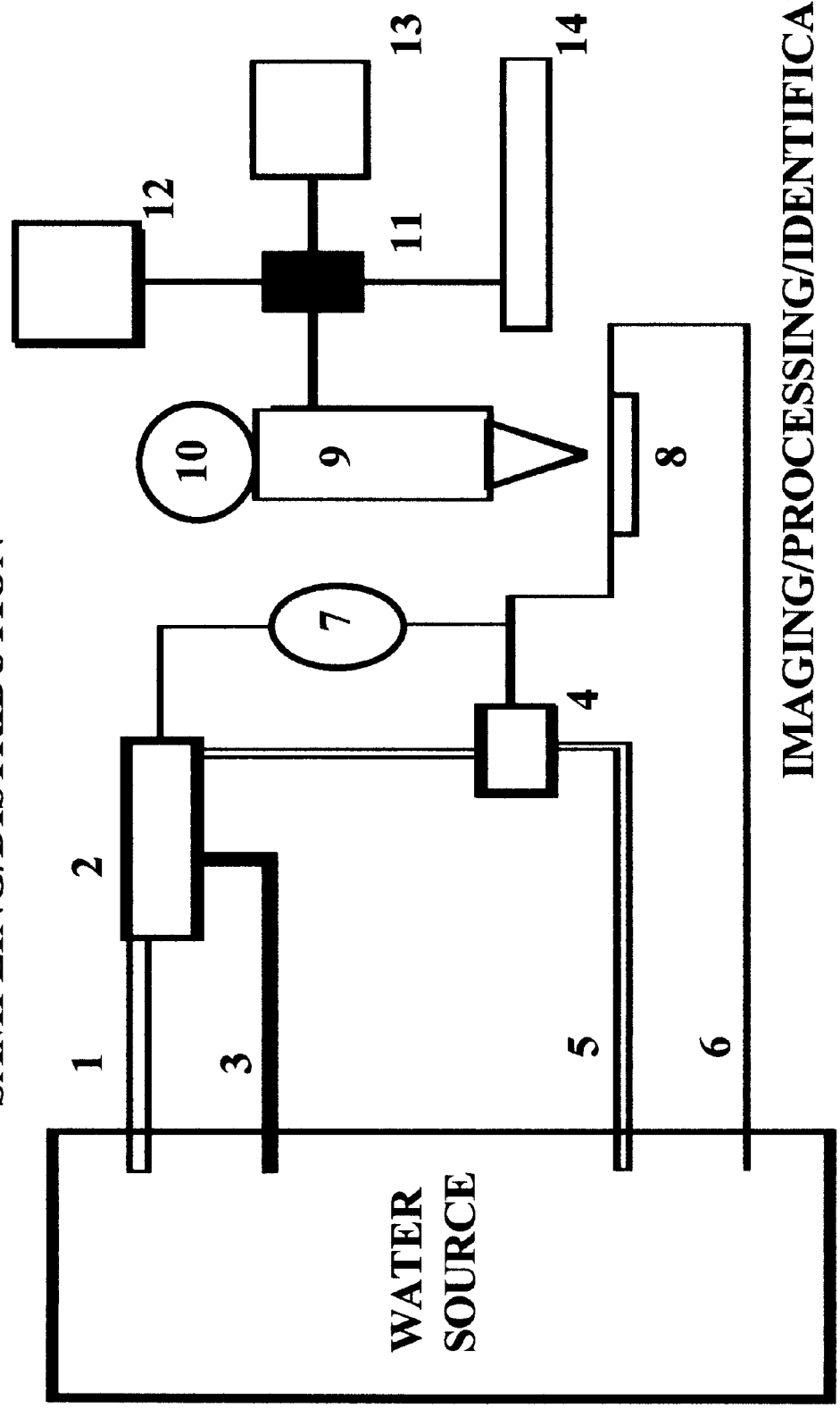

CONTINUOUS MICROBIOTAL RECOGNITION METHOD

CROSS REFERENCE TO RELATED APPLICATIONS:

| U.S. Pat. Documents | | |
|---|---|---|
| 5,627,907 | May 6, 1997 | Gur, et. al. |
| 5,561,718 | Oct. 1, 1996 | Trew, et. al. |
| 5,550,933 | Aug. 27, 1996 | Stetten |
| 5,544,265 | Aug. 6, 1996 | Bozinovic, et. al. |
| 5,313,532 | May 17, 1994 | Harvey, et. al. |
| 5,224,036 | Jun. 29, 1993 | Ito, et. al. |
| 5,638,459 | Jun. 10, 1997 | Rosenlof, et. al. |
| 4,199,748 | Apr. 22, 1980 | Bacus |
| 4,821,336 | Apr. 11, 1989 | Roye |

OTHER PUBLICATIONS

Aloimonos, J. Visual Shape Computation, Proceedings of the IEEE, vol. 76, pp. 899–916, August 1988.

Bartels, Peter H. et al., "A Self-Learning Computer Program for Cell Recognition", ACTA Cytologica: The Journal of Clinical Cytology, 14:8, pp. 486–494, October 1970.

Brailsford, M. and S. Gatley 1993. Rapid analysis of microorganisms using flow cytometry. in: Lloyd, D. ed. 1993. *Flow Cytometry in Microbiology.* Springer Verlag, London.

Cooke-Yarborough et al., "The Automatic Counting of Red Blood Cells", British Journal of Applied Physics, Supp. #3, 1954, pp. 147–156.

Das, M. F. Butterworth, and R. Das. 1996. Statistical signal modeling techniques for automated recognition of water-borne microbial shapes. Proc. 39th Midwest Symposium on Circuits and Systems pp. 613–616. IEEE Press, Piscataway.

Kiryati, N. Calculating Geometric Properties of objects Represented by Fourier Coefficients of Boundary Functions. IEEE Conference on Computer Vision and Pattern Recognition, 1988, Ann Arbor, US, pp.641–646.

Mukawa, A. et al., Progress Report on Experimental Use of CYBEST Model 2 for Practical Gynecologic Mass Screening. pp. 31–34, March 1983.

Porter, J., , J. Robinson, C. Edwards, 1995 Recovery of a bacterial sub-population from sewage using immunofluorescent flow cytometry and cell sorting. FEMS microbiology letters. 133 (n $1/2$): 195.

Shen, et al, Application of Shape Analysis to Mammographic Calcifications, IEEE: Transactions on Medial Imaging June 1994, vol. 13, No. 2, pp. 263–274.

Sprules, W. G., B. Bergstrom, H. Cyr, B. R. Hargreaves, S. S. Kilham, H. J. MacIsaac, K. Matsushita, R. S. Stemberger, R. Williams. 1992. Non-video optical instruments for studying zooplankton distribution and abundance. Arch. Hydrobiol. Beih., 36:45–58.

Wied, G.L. et al., "Expert Systems as Classifiers in Diagnostic Cytopathology", IEEE/NinthAnnual Conference of the Engineering in Medicine and Biology Society, pp. 1915–1917,.COPYRGT.1987.

Zhu et al, A Transforrnation Invariant Recursive Subdivision Method for Shape Analysis. IEEE Proceedings of the 9th International Conference on Pattern Recognition, vol. 2, Nov.17, 1988 pp. 833–835.

STATEMENT REGARDING FEDERALLY SPONSORED RESEARCH OR DEVELOPMENT

The work on the said invention was not supported by federally-sponsored research finds.

REFERENCE TO A MICROFICHE APPENDIX

Not applicable.

BACKGROUND OF THE INVENTION

Field of Invention: The present invention is a new method for monitoring water for microbiota. Specific organisms are identified optically and electronically in a continuous, real-time process usmg specific, customized software and commercially available equipment. The method will archive analog and digital images of the organisms. The type and frequency of the identified water-borne organisms will be immediately employed to alter wastewater treatment processes or to close drinking water intake pipes.

Description of Prior Art: Other technology that can use continuous, real-time analysis is of two basic types. One method is based on the size of the organism (particle counters), and the other is based on fluorescence of the organism (flow cytometers). Particle counters have serious limitations because they can only distinguish a narrow range of sizes and they cannot distinguish the type of organisms within the size range (Sprules et al., 1992). Also there is no way to distinguish inanimate particles from living organisms. A commercially available counter is the Optical Plankton Counter Model OPC-LT, OPC-IL, OPC-2D by Focal Technologies, Inc. Dartmouth, Nova Scotia.

The flow cytometry machines utilize fluorescence to identify the organisms either through autofluorescence the wavelength of which would be specific for the organism or through specific fluorochrome dyes linked to antibodies that are organism specific (Brailsford and Gatley, 1993). With this system specific identification can be made, but only if the organism autofluoresces at its specific wavelength. If it does not autofluoresce, fluorochrome-antibody complexes have to be made for a specific organism. Thus the flow cytometry system is very limited: limited to the organisms that emit specific wavelengths, if they autofluoresce, and limited by the necessity to make specific antibodies to a very large variety and range of organisms to anticipate the available organisms. Thus the increase in specificity comes with a decrease in speed, over the particle counter. Further, the machine is extremely expensive, approximately 10 times greater than our method. It is also much more expensive to maintain and operate. A commercially available machine is made by Coulter, model EPICS 741.

To overcome some of the drawbacks, a combination of the two technologies (looking at fluorescence of the particles) has been tried (Porter et al., 1995). Thus there is an increase in specificity and decrease in speed over the standard particle counter. A commercially available machine is the Becton Dickenson FACStar Plus. But the immunofluorescent flow cytometry/ particle counter system is still a particle counter that makes identification indirectly, that requires great expertise and cost to operate, and will be difficult to operate in real time.

The current invention, the Continuous Microbiotal Recognition Method is superior to the above technology. High specificity is obtained with phase microscope images coupled with software to identify specific organisms makes this technology relatively fast speed and relatively low cost (Das et al., 1996).

References Cited

Brailsford, M. and S. Gatley 1993. Rapid analysis of microorganisms using flow cytometry. in: Lloyd, D. ed. 1993. Flow Cytometry in Microbiology. Springer Verlag, London.

Das, M, F. Butterworth, and R. Das. 1996. Statistical signal modeling techniques for automated recognition of water-borne microbial shapes. Proc. 39th Midwest Symposium on Circuits and Systems pp. 613–616. IEEE Press, Piscataway.

Porter, J., , J. Robinson, C. Edwards, 1995 Recovery of a bacterial sub-population from sewage using immunofluorescent flow cytometry and cell sorting. FEMS microbiology letters. 133 (n ½):195.

Sprules, W. G., B. Bergstrom, H. Cyr, B. R. Hargreaves, S. S. Kilham, H. J. MacIsaac, K. Matsushita, R. S. Stemberger, R. Williams. 1992. Non-video optical instruments for studying zooplankton distribution and abundance. Arch. Hydrobiol. Beih., 36:45"58.

BRIEF SUMMARY OF THE INVENTION

The method is an automated, continuous, opto-electronic system designed to recognize and identify microbiota in water with the purpose of assessing (1) the quality and extent of sewage digestion, (2) the presence of pathogens in drinking water, and (3) the biological status of natural waters. It involves two separate stages: sampling/distribution and imaging/processing/identification. First, the water to be tested is pumped into the sampling/distribution part of the Continuous Microbiotal Recognition system where aliquots are moved into a viewing chamber of a microscope. In the second stage, microbiota will be imaged by video, the images will be captured digitally, and a CPU with peripheral and I/O devices will process, archive and act on this captured information. The images will be processed where decisions based on a fuzzy decision tree in the CPU can be made to issue warnings to personnel and/or commands to close or open valves, transmitted via modem and phone lines/local area networks, by an actuator/annunciator device.

Thus the Continuous Microbiotal Recognition Method is superior to the particle counting, flow cytometry or combined methods because it is able to identify specific organisms, over a wider range of sizes and categories, in real time with far greater certainty, at far less cost.

BRIEF DESCRIPTION THE DRAWING

The drawing 1—1 illustrates the method which involves two general parts: sampling /distribution and imaging/processing/identification. In the first part the water to be tested is pumped into the system at (1) uptake tube and through check valves where it enters the sampler (2). Here, the sample is drawn by a small peristaltic pump (4) to the microscopic viewing chamber (8). The excess test water returns to the water source through tubes (3), (5), and (6). The entire system can be rinsed with filtered water from a pump and reservoir (7). The second part of the method involves capturing microscopic images of microbiota in the viewing chamber (8) with a compound, phase-optical microscope (9) and CCD/video camera (10) and the CPU with peripheral and I/O devices (11). Here, images are processed, archived in a digital storage device (12) and statistical information concerning cell numbers per class, proportions of cell classes throughout the entire process is stored in a numerical database (13). Decisions derived from a rule-based expert system in the CPU (1 1) are made issuing warnings and commands transmitted internally via cables to (2), (4), and (7) and externally via modem and phone lines/local area networks by an actuator/annunciator device (14).

DETAILED DESCRIPTION OF THE INVENTION a. Sample collection and distribution:

Water volumes will be collected from the water source using standard, commercially available, automated, sample-collection systems such as Model PS 600 available from Manning Experimental, Georgetown TX. Water will be pumped peristaltically with a commercially-available pump into the viewing chamber, a commercially-available flat, optical glass, tube for viewing the microscopic contents of the water. All steps in this sample collection/distribution stage will be controlled by a programmable computer controller. A small, commercial peristaltic pump will pump fresh, filtered water to remove the test water and at the same time rinse the microscopic viewing chamber. Different magnifications will utilize different microscopes dedicated to that magnification and require special optics and lighting conditions. Water samples will be pumped simultaneously and continuously into a microscope viewing chamber for each microscope used.

b. Imaging, processing and identification:

Images will be captured and archived on video tape and transferred to a digital storage device. Archived tapes will be available for the chronological history of the sampling steps. Images captured by the CCD camera will be digitized and processed before classification. Software triggered by motion and field detectors will characterize the field contents and make preliminary identifications. The image processing operations consist of cleaning and restoration, which will remove noise and extraneous objects from the image frames by using novel edge-preserving restoration and enhancement techniques. Next the processed image will be segmented, and the segmented images will undergo feature extraction including morphological, color, and motion features. Next, in a recognition/classification step extracted features will be used to search a digital image database in a hierarchical fashion for matching specific microbiota-class profiles. The hierarchical search works by first narrowing the search to one of several groups. Then, within a group it searches for one of the several subclasses. Once identified and assigned to a class, the numbers of cells in a class are stored as a cell concentration profile. An improved rule-based expert system or flizzy decision tree at preset intervals will evaluate the proportion of all cell classes. Finally, in the actuator/annunciator step commands and controls based on the biological status of the water will trigger relays that will issue valving commands and warnings and reports through modem lines or local area networks. Images of microbiota collected in the above automated system will be stored for future evaluation and enumeration purposes

What is claimed is:

1. A method of continuously recognizing microbiota in various types of water, including sewage, river and drinking water, comprising the steps of:

performing random sampling of a water source using an aquatic sampling apparatus;

passing the sampled water through a mesh filter and diverting a smaller sample of the water into a tube using a peristaltic pump;

conveying the smaller sample of water into a microscope viewing chamber and optical plane using said tube and said peristaltic pump;

capturing images in said optical plane using a CCD/video camera; wherein said images are recorded for analogue storage;

digitizing said images for processing and chronological storage;

filtering the digitized images to remove extraneous objects and noise using edge-preserving image restoration and enhancement software;

segmenting the filtered images;

extracting morphological-, color-, and motion-related features from the segmented images;

classifying microbiota in the images by searching a database in a hierarchical fashion using the extracted features to match specific microbiotal class profiles;

constructing estimated cell concentration profiles for different microbiotal classes using the classification results obtained from N consecutive image frames;

monitoring the estimated cell concentration profiles at regular time intervals using a rule-based expert system to scan a fuzzy decision tree; and generating appropriate command and control signals and transmitting these signals to alarm and actuating devices by means of cables and local area network or modem connections.

* * * * *